United States Patent
Tsun et al.

(10) Patent No.: US 10,597,454 B2
(45) Date of Patent: Mar. 24, 2020

(54) PD-1 ANTIBODIES

(71) Applicant: INNOVENT BIOLOGICS (SUZHOU) CO., LTD, Suzhou (CN)

(72) Inventors: Andy Tsun, Suzhou (CN); Cheng Chen, Suzhou (CN); Xiaolin Liu, Suzhou (CN); De-Chao Michael Yu, Suzhou (CN)

(73) Assignee: INNOVENT BIOLOGICS (SUZHOU) CO., LTD, Suzhou (CN)

( * ) Notice: Subject to any disclaimer, the term of this patent is extended or adjusted under 35 U.S.C. 154(b) by 1 day.

(21) Appl. No.: 16/064,727

(22) PCT Filed: Oct. 15, 2016

(86) PCT No.: PCT/CN2016/102238
§ 371 (c)(1),
(2) Date: Jun. 21, 2018

(87) PCT Pub. No.: WO2018/068336
PCT Pub. Date: Apr. 19, 2018

(65) Prior Publication Data
US 2019/0023792 A1    Jan. 24, 2019

(51) Int. Cl.
*C07K 16/28* (2006.01)
*A61P 35/00* (2006.01)
*A61K 39/395* (2006.01)
*A61K 38/16* (2006.01)

(52) U.S. Cl.
CPC ........ *C07K 16/2818* (2013.01); *A61K 39/395* (2013.01); *A61P 35/00* (2018.01); *A61K 38/16* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | 2012177624 A2 | 12/2012 |
|---|---|---|
| WO | 2013/079174 A1 | 6/2013 |
| WO | 2013/173223 A1 | 11/2013 |
| WO | 2013/181452 A1 | 12/2013 |

OTHER PUBLICATIONS

Mariuzza, R.A. etal. 'The Structural Basis of Antigen-Antibody Recognition1 Annu. Rev. Biophys. Biphys. Chem. 16:139-159, 1987.*
MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. 'Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
International Search Report (ISR) and Written Opinion (WO) dated Jul. 13, 2017 for International Application No. PCT /CN2016/ 102238.

* cited by examiner

*Primary Examiner* — Nora M Rooney
(74) *Attorney, Agent, or Firm* — Ladas & Parry LLP

(57) ABSTRACT

The present invention provides antibodies that bind human programmed cell death 1 (PD-1), and may be useful for treating cancer alone and in combination with chemotherapy and other cancer therapeutics.

20 Claims, No Drawings
Specification includes a Sequence Listing.

SEQUENCE LISTING

<160> NUMBER OF SEQ ID NOS: 30

<210> SEQ ID NO 1
<211> LENGTH: 288
<212> TYPE: PRT
<213> ORGANISM: artificial sequence
<220> FEATURE:
<223> OTHER INFORMATION: PD-1

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

-continued

```
Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 2
<211> LENGTH: 13
<212> TYPE: PRT
<213> ORGANISM: artificial sequence
<220> FEATURE:
<223> OTHER INFORMATION: HCDR1 of xd-16 A, xd-16 B, xd-16 C, xd-16 D,
      and xd-16 E

<400> SEQUENCE: 2

```
Lys Ala Ser Gly Gly Thr Phe Ser Ser Thr Ala Ile Ser
1               5                   10
```

<210> SEQ ID NO 3
<211> LENGTH: 17
<212> TYPE: PRT
<213> ORGANISM: artificial sequence
<220> FEATURE:
<223> OTHER INFORMATION: HCDR2 of xd-16 A

<400> SEQUENCE: 3

```
Gly Ile Trp Pro Ser Phe Gly Thr Ala Asn Tyr Ala Gln Lys Phe Gln
1               5                   10                  15

Gly
```

<210> SEQ ID NO 4
<211> LENGTH: 17
<212> TYPE: PRT

<213> ORGANISM: artificial sequence
<220> FEATURE:
<223> OTHER INFORMATION: HCDR2 of xd-16 B

<400> SEQUENCE: 4

Gly Ile Trp Pro Ser Phe Gly Thr Ala Ser Tyr Ala Gln Lys Phe Gln
1               5                   10                  15

Gly

<210> SEQ ID NO 5
<211> LENGTH: 17
<212> TYPE: PRT
<213> ORGANISM: artificial sequence
<220> FEATURE:
<223> OTHER INFORMATION: HCDR2 of xd-16 C

<400> SEQUENCE: 5

Gly Ile Trp Pro Ser Phe Gly Thr Ala Ser Tyr Ala Gln Lys Phe Arg
1               5                   10                  15

Gly

<210> SEQ ID NO 6
<211> LENGTH: 17
<212> TYPE: PRT
<213> ORGANISM: artificial sequence
<220> FEATURE:
<223> OTHER INFORMATION: HCDR2 of xd-16 D

<400> SEQUENCE: 6

Gly Ile Trp Pro Ser Phe Asp Thr Ala Asn Tyr Ala Gln Lys Phe Arg
1               5                   10                  15

Gly

<210> SEQ ID NO 7
<211> LENGTH: 17
<212> TYPE: PRT
<213> ORGANISM: artificial sequence
<220> FEATURE:
<223> OTHER INFORMATION: HCDR2 of xd-16 E

<400> SEQUENCE: 7

Gly Ile Trp Pro Ser Phe Gly Thr Ala Asn Tyr Ala Arg Lys Phe Gln
1               5                   10                  15

Gly

<210> SEQ ID NO 8
<211> LENGTH: 13
<212> TYPE: PRT
<213> ORGANISM: artificial sequence
<220> FEATURE:
<223> OTHER INFORMATION: HCDR3 of xd-16 A, xd-16 C, xd-16 D

<400> SEQUENCE: 8

Ala Arg Ala Glu Tyr Ser Ser Thr Gly Thr Phe Asp Tyr
1               5                   10

<210> SEQ ID NO 9
<211> LENGTH: 13
<212> TYPE: PRT
<213> ORGANISM: artificial sequence
<220> FEATURE:
<223> OTHER INFORMATION: HCDR3 of xd-16 B, xd-16 E

<400> SEQUENCE: 9

```
Ala Arg Ala Glu Tyr Ser Ser Thr Gly Ile Phe Asp Tyr
 1               5                  10
```

<210> SEQ ID NO 10
<211> LENGTH: 11
<212> TYPE: PRT
<213> ORGANISM: artificial sequence
<220> FEATURE:
<223> OTHER INFORMATION: LCDR1 of xd-16 A, xd-16 B, xd-16 C, xd-16 D,
      and xd-16 E

<400> SEQUENCE: 10

```
Arg Ala Ser Gln Gly Ile Ser Ser Trp Leu Ala
 1               5                  10
```

<210> SEQ ID NO 11
<211> LENGTH: 8
<212> TYPE: PRT
<213> ORGANISM: artificial sequence
<220> FEATURE:
<223> OTHER INFORMATION: LCDR2 of xd-16 A, xd-16 B, xd-16 C, xd-16 D,
      and xd-16 E

<400> SEQUENCE: 11

```
Ser Ala Ala Ser Ser Leu Gln Ser
 1               5
```

<210> SEQ ID NO 12
<211> LENGTH: 9
<212> TYPE: PRT
<213> ORGANISM: artificial sequence
<220> FEATURE:
<223> OTHER INFORMATION: LCDR3 of xd-16 A, xd-16 B, xd-16 C, xd-16 D,
      and xd-16 E

<400> SEQUENCE: 12

```
Gln Gln Ala Asn His Leu Pro Phe Thr
 1               5
```

<210> SEQ ID NO 13
<211> LENGTH: 120
<212> TYPE: PRT
<213> ORGANISM: artificial sequence
<220> FEATURE:
<223> OTHER INFORMATION: HCVR of xd-16 A

<400> SEQUENCE: 13

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Thr
             20                  25                  30

Ala Ile Ser Trp Val Arg Gln Ala Pro Gly Gln Gly Leu Glu Trp Met
         35                  40                  45

Gly Gly Ile Trp Pro Ser Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Glu Tyr Ser Ser Thr Gly Thr Phe Asp Tyr Trp Gly Gln
                100                 105                 110

Gly Thr Leu Val Thr Val Ser Ser
            115                 120
```

```
<210> SEQ ID NO 14
<211> LENGTH: 120
<212> TYPE: PRT
<213> ORGANISM: artificial sequence
<220> FEATURE:
<223> OTHER INFORMATION: HCVR of xd-16 B

<400> SEQUENCE: 14
```

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 |     |     |     | 5   |     |     |     |     | 10  |     |     |     |     | 15  |     |

| Ser | Val | Lys | Val | Ser | Cys | Lys | Ala | Ser | Gly | Gly | Thr | Phe | Ser | Ser | Thr |
|---|---|---|---|---|---|---|---|---|---|---|---|---|---|---|---|
|     |     |     | 20  |     |     |     |     | 25  |     |     |     |     | 30  |     |     |

| Ala | Ile | Ser | Trp | Val | Arg | Gln | Ala | Pro | Gly | Gln | Gly | Leu | Glu | Trp | Met |
|---|---|---|---|---|---|---|---|---|---|---|---|---|---|---|---|
|     |     | 35  |     |     |     |     | 40  |     |     |     |     | 45  |     |     |     |

| Gly | Gly | Ile | Trp | Pro | Ser | Phe | Gly | Thr | Ala | Ser | Tyr | Ala | Gln | Lys | Phe |
|---|---|---|---|---|---|---|---|---|---|---|---|---|---|---|---|
|     | 50  |     |     |     |     | 55  |     |     |     |     | 60  |     |     |     |     |

| Gln | Gly | Arg | Val | Thr | Ile | Thr | Ala | Asp | Glu | Ser | Thr | Ser | Thr | Ala | Tyr |
|---|---|---|---|---|---|---|---|---|---|---|---|---|---|---|---|
| 65  |     |     |     |     | 70  |     |     |     |     | 75  |     |     |     |     | 80  |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
|     |     |     |     | 85  |     |     |     |     | 90  |     |     |     |     | 95  |     |

| Ala | Arg | Ala | Glu | Tyr | Ser | Ser | Thr | Gly | Ile | Phe | Asp | Tyr | Trp | Gly | Gln |
|---|---|---|---|---|---|---|---|---|---|---|---|---|---|---|---|
|     |     |     | 100 |     |     |     |     | 105 |     |     |     |     | 110 |     |     |

| Gly | Thr | Leu | Val | Thr | Val | Ser | Ser |
|---|---|---|---|---|---|---|---|
|     |     | 115 |     |     |     |     | 120 |

```
<210> SEQ ID NO 15
<211> LENGTH: 120
<212> TYPE: PRT
<213> ORGANISM: artificial sequence
<220> FEATURE:
<223> OTHER INFORMATION: HCVR of xd-16 C

<400> SEQUENCE: 15
```

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 |     |     |     | 5   |     |     |     |     | 10  |     |     |     |     | 15  |     |

| Ser | Val | Lys | Val | Ser | Cys | Lys | Ala | Ser | Gly | Gly | Thr | Phe | Ser | Ser | Thr |
|---|---|---|---|---|---|---|---|---|---|---|---|---|---|---|---|
|     |     |     | 20  |     |     |     |     | 25  |     |     |     |     | 30  |     |     |

| Ala | Ile | Ser | Trp | Val | Arg | Gln | Ala | Pro | Gly | Gln | Gly | Leu | Glu | Trp | Met |
|---|---|---|---|---|---|---|---|---|---|---|---|---|---|---|---|
|     |     | 35  |     |     |     |     | 40  |     |     |     |     | 45  |     |     |     |

| Gly | Gly | Ile | Trp | Pro | Ser | Phe | Gly | Thr | Ala | Ser | Tyr | Ala | Gln | Lys | Phe |
|---|---|---|---|---|---|---|---|---|---|---|---|---|---|---|---|
|     | 50  |     |     |     |     | 55  |     |     |     |     | 60  |     |     |     |     |

| Arg | Gly | Arg | Val | Thr | Ile | Thr | Ala | Asp | Glu | Ser | Thr | Ser | Thr | Ala | Tyr |
|---|---|---|---|---|---|---|---|---|---|---|---|---|---|---|---|
| 65  |     |     |     |     | 70  |     |     |     |     | 75  |     |     |     |     | 80  |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
|     |     |     |     | 85  |     |     |     |     | 90  |     |     |     |     | 95  |     |

| Ala | Arg | Ala | Glu | Tyr | Ser | Ser | Thr | Gly | Thr | Phe | Asp | Tyr | Trp | Gly | Gln |
|---|---|---|---|---|---|---|---|---|---|---|---|---|---|---|---|
|     |     |     | 100 |     |     |     |     | 105 |     |     |     |     | 110 |     |     |

| Gly | Thr | Leu | Val | Thr | Val | Ser | Ser |
|---|---|---|---|---|---|---|---|
|     |     | 115 |     |     |     |     | 120 |

```
<210> SEQ ID NO 16
<211> LENGTH: 120
<212> TYPE: PRT
<213> ORGANISM: artificial sequence
<220> FEATURE:
<223> OTHER INFORMATION: HCVR of xd-16 D

<400> SEQUENCE: 16
```

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|

```
                1               5                  10                  15
        Ser Val Lys Val Ser Cys Lys Ala Ser Gly Gly Thr Phe Ser Ser Thr
                        20                  25                  30

Ala Ile Ser Trp Val Arg Gln Ala Pro Gly Gln Gly Leu Glu Trp Met
                        35                  40                  45

Gly Gly Ile Trp Pro Ser Phe Asp Thr Ala Asn Tyr Ala Gln Lys Phe
                        50                  55                  60

Arg Gly Arg Val Thr Ile Thr Ala Asp Glu Ser Thr Ser Thr Ala Tyr
        65                      70                  75                  80

Met Glu Leu Ser Ser Leu Arg Ser Glu Asp Thr Ala Val Tyr Tyr Cys
                        85                  90                  95

Ala Arg Ala Glu Tyr Ser Ser Thr Gly Thr Phe Asp Tyr Trp Gly Gln
                        100                 105                 110

Gly Thr Leu Val Thr Val Ser Ser
                        115                 120

<210> SEQ ID NO 17
<211> LENGTH: 120
<212> TYPE: PRT
<213> ORGANISM: artificial sequence
<220> FEATURE:
<223> OTHER INFORMATION: HCVR of xd-16 E

<400> SEQUENCE: 17

Gln Val Gln Leu Val Gln Ser Gly Ala Glu Val Lys Lys Pro Gly Ser
        1               5                   10                  15

Ser Val Lys Val Ser Cys Lys Ala Ser Gly Gly Thr Phe Ser Ser Thr
                        20                  25                  30

Ala Ile Ser Trp Val Arg Gln Ala Pro Gly Gln Gly Leu Glu Trp Met
                        35                  40                  45

Gly Gly Ile Trp Pro Ser Phe Gly Thr Ala Asn Tyr Ala Arg Lys Phe
                        50                  55                  60

Gln Gly Arg Val Thr Ile Thr Ala Asp Glu Ser Thr Ser Thr Ala Tyr
        65                      70                  75                  80

Met Glu Leu Ser Ser Leu Arg Ser Glu Asp Thr Ala Val Tyr Tyr Cys
                        85                  90                  95

Ala Arg Ala Glu Tyr Ser Ser Thr Gly Ile Phe Asp Tyr Trp Gly Gln
                        100                 105                 110

Gly Thr Leu Val Thr Val Ser Ser
                        115                 120

<210> SEQ ID NO 18
<211> LENGTH: 107
<212> TYPE: PRT
<213> ORGANISM: artificial sequence
<220> FEATURE:
<223> OTHER INFORMATION: LCVR of xd-16 A, xd-16 B, xd-16 C, xd-16 D,
      and xd-16 E

<400> SEQUENCE: 18

Asp Ile Gln Met Thr Gln Ser Pro Ser Ser Val Ser Ala Ser Val Gly
        1               5                   10                  15

Asp Arg Val Thr Ile Thr Cys Arg Ala Ser Gln Gly Ile Ser Ser Trp
                        20                  25                  30

Leu Ala Trp Tyr Gln Gln Lys Pro Gly Lys Ala Pro Lys Leu Leu Ile
                        35                  40                  45

Ser Ala Ala Ser Ser Leu Gln Ser Gly Val Pro Ser Arg Phe Ser Gly
                        50                  55                  60
```

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105

<210> SEQ ID NO 19
<211> LENGTH: 447
<212> TYPE: PRT
<213> ORGANISM: artificial sequence
<220> FEATURE:
<223> OTHER INFORMATION: HC of xd-16 A - S228P IgG4

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Thr
                20                  25                  30

Ala Ile Ser Trp Val Arg Gln Ala Pro Gly Gln Gly Leu Glu Trp Met
            35                  40                  45

Gly Gly Ile Trp Pro Ser Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Thr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 20
<211> LENGTH: 447
<212> TYPE: PRT
<213> ORGANISM: artificial sequence
<220> FEATURE:
<223> OTHER INFORMATION: HC of xd-16 B- S228P IgG4

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Thr
            20                  25                  30

Ala Ile Ser Trp Val Arg Gln Ala Pro Gly Gln Gly Leu Glu Trp Met
        35                  40                  45

Gly Gly Ile Trp Pro Ser Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Ile Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 21
<211> LENGTH: 447
<212> TYPE: PRT
<213> ORGANISM: artificial sequence
<220> FEATURE:
<223> OTHER INFORMATION: HC of xd-16 C- S228P IgG4

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Thr
            20                  25                  30

Ala Ile Ser Trp Val Arg Gln Ala Pro Gly Gln Gly Leu Glu Trp Met
        35                  40                  45

Gly Gly Ile Trp Pro Ser Phe Gly Thr Ala Ser Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

-continued

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 22
<211> LENGTH: 447
<212> TYPE: PRT
<213> ORGANISM: artificial sequence
<220> FEATURE:
<223> OTHER INFORMATION: HC of xd-16 D- S228P IgG4

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Thr
            20                  25                  30

Ala Ile Ser Trp Val Arg Gln Ala Pro Gly Gln Gly Leu Glu Trp Met
            35                  40                  45

Gly Gly Ile Trp Pro Ser Phe Asp Thr Ala Asn Tyr Ala Gln Lys Phe
        50                  55                  60

Arg Gly Arg Val Thr Ile Thr Ala Asp Glu Ser Thr Ser Thr Ala Tyr
65                  70                  75                  80

-continued

```
Met Glu Leu Ser Ser Leu Arg Ser Glu Asp Thr Ala Val Tyr Tyr Cys
                85                  90                  95

Ala Arg Ala Glu Tyr Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 23
<211> LENGTH: 447
<212> TYPE: PRT
<213> ORGANISM: artificial sequence
<220> FEATURE:
<223> OTHER INFORMATION: HC of xd-16 E- S228P IgG4

<400> SEQUENCE: 23

```
Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Thr
            20                  25                  30

Ala Ile Ser Trp Val Arg Gln Ala Pro Gly Gln Gly Leu Glu Trp Met
        35                  40                  45

Gly Gly Ile Trp Pro Ser Phe Gly Thr Ala Asn Tyr Ala Arg Lys Phe
    50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Ile Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 24
<211> LENGTH: 214
<212> TYPE: PRT
<213> ORGANISM: artificial sequence
<220> FEATURE:
<223> OTHER INFORMATION: LC of xd-16 A, xd-16 B, xd-16 C, xd-16 D, and
      xd-16 E

<400> SEQUENCE: 24

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 1347
<212> TYPE: DNA
<213> ORGANISM: artificial sequence
<220> FEATURE:
<223> OTHER INFORMATION: HC of xd-16 A S228P IgG4

<400> SEQUENCE: 25
caggtgcagc tggtgcagtc tggggctgag gtgaagaagc ctgggtcctc ggtgaaggtc      60
tcctgcaagg cttctggagg caccttcagc agcactgcta tcagctgggt gcgacaggcc     120
cctggacaag gcttgagtg gatgggaggg atctggccta gttttggtac agcaaactac     180
gcacagaagt tccagggcag agtcacgatt accgcgacg aatccacgag cacagcctac     240
atggagctga gcagcctgag atctgaggac acggcggtgt actactgcgc aagagccgag     300

```
tacagtagca caggaaccctt tgattactgg ggacagggta cattggtcac cgtctcctca    360
gcttccacaa aaggcccccag cgtgtttccc ctggcccctt gtagcaggtc cacctccgaa    420
agcacagccg ctctgggctg cctggtcaag gattacttcc ccgagcccgt gaccgtgtcc    480
tggaatagcg gcgctctcac atccggagtg catacctttc ctgccgtgct ccagtcctcc    540
ggcctgtact ccctgagctc cgtggtgacc gtcccttcca gctccctggg caccaagacc    600
tatacctgta acgtggacca caagcccctcc aataccaagg tggataagcg ggtcgagtcc    660
aagtacggac ccccttgccc tccttgtcct gctcctgaat tcctcggcgg acctagcgtc    720
tttctcttcc cccccaagcc caaggatacc ctgatgatct ccaggacccc cgaggtgaca    780
tgcgtcgtgg tcgatgtgtc ccaggaggat cctgaagtgc agttcaactg gtacgtggac    840
ggcgtcgaag tgcataacgc caagaccaag cccaggagg agcagttcaa ctccacctat    900
cgggtggtga gcgtgctgac cgtgctgcat caggactggc tcaacggcaa agagtacaag    960
tgcaaggtct ccaacaaggg actccccctcc agcatcgaga agaccattag caaggccaaa   1020
ggccaaccca gggagcctca ggtatatacg ctgcccccca gccaggagga gatgaccaaa   1080
aaccaggtca gcctcacctg tctggtcaag ggcttctacc ctagcgacat tgctgtcgag   1140
tgggagagca acggccagcc cgagaacaac tataaaacca ccccccctgt cctggactcc   1200
gacggatcct tcttcctgta ctccaggctg acagtcgaca gtcccggtg gcaagaggga   1260
aacgtcttct cctgctccgt gatgcacgaa gctctccaca ccactacac ccagaagagc   1320
ctcagcctgt ccctgggcaa atgatga                                       1347
```

<210> SEQ ID NO 26
<211> LENGTH: 1347
<212> TYPE: DNA
<213> ORGANISM: artificial sequence
<220> FEATURE:
<223> OTHER INFORMATION: HC of xd-16 B S228P IgG4

<400> SEQUENCE: 26

```
caggtgcagc tggtgcagtc tggggctgag gtgaagaagc ctgggtcctc ggtgaaggtc     60
tcctgcaagg cttctggagg caccttcagc agcactgcta tcagctgggt gcgacaggcc    120
cctggacaag gcttgagtg gatgggaggg atctggccta gttttggtac agcaagctac    180
gcacagaagt tccagggcag agtcacgatt accgcggacg aatccacgag cacagcctac    240
atggagctga gcagcctgag atctgaggac acggcggtgt actactgcgc aagagccgag    300
tacagtagca caggaatctt tgattactgg ggacagggta cattggtcac cgtctcctca    360
gcttccacaa aaggcccccag cgtgtttccc ctggcccctt gtagcaggtc cacctccgaa    420
agcacagccg ctctgggctg cctggtcaag gattacttcc ccgagcccgt gaccgtgtcc    480
tggaatagcg gcgctctcac atccggagtg catacctttc ctgccgtgct ccagtcctcc    540
ggcctgtact ccctgagctc cgtggtgacc gtcccttcca gctccctggg caccaagacc    600
tatacctgta acgtggacca caagcccctcc aataccaagg tggataagcg ggtcgagtcc    660
aagtacggac ccccttgccc tccttgtcct gctcctgaat tcctcggcgg acctagcgtc    720
tttctcttcc cccccaagcc caaggatacc ctgatgatct ccaggacccc cgaggtgaca    780
tgcgtcgtgg tcgatgtgtc ccaggaggat cctgaagtgc agttcaactg gtacgtggac    840
ggcgtcgaag tgcataacgc caagaccaag cccaggagg agcagttcaa ctccacctat    900
cgggtggtga gcgtgctgac cgtgctgcat caggactggc tcaacggcaa agagtacaag    960
tgcaaggtct ccaacaaggg actccccctcc agcatcgaga agaccattag caaggccaaa   1020
```

```
ggccaaccca gggagcctca ggtatatacg ctgcccccca gccaggagga gatgaccaaa      1080
aaccaggtca gcctcacctg tctggtcaag ggcttctacc ctagcgacat tgctgtcgag      1140
tgggagagca acggccagcc cgagaacaac tataaaacca ccccccctgt cctggactcc      1200
gacggatcct tcttcctgta ctccaggctg acagtcgaca agtcccggtg gcaagaggga      1260
aacgtcttct cctgctccgt gatgcacgaa gctctccaca accactacac ccagaagagc      1320
ctcagcctgt ccctgggcaa atgatga                                         1347

<210> SEQ ID NO 27
<211> LENGTH: 1347
<212> TYPE: DNA
<213> ORGANISM: artificial sequence
<220> FEATURE:
<223> OTHER INFORMATION: HC of xd-16 C S228P IgG4

<400> SEQUENCE: 27
caggtgcagc tggtgcagtc tggggctgag gtgaagaagc ctgggtcctc ggtgaaggtc        60
tcctgcaagg cttctggagg caccttcagc agcactgcta tcagctgggt gcgacaggcc       120
cctggacaag gcttgagtg gatgggaggg atctggccta gttttggtac agcaagctac        180
gcacagaagt tccggggcag agtcacgatt accgcggacg aatccacgag cacagcctac       240
atggagctga gcagcctgag atctgaggac acggcggtgt actactgcgc aagagccgag       300
tacagtagca caggaaccct tgattactgg ggacaggta cattggtcac cgtctcctca       360
gcttccacaa aggcccccag cgtgtttccc ctggccccct tgtagcaggtc cacctccgaa       420 agcacagccg ctctgggctg cctggtcaag gattacttcc ccgagcccgt gaccgtgtcc       480
tggaatagcg gcgctctcac atccggagtg catacctttc ctgccgtgct ccagtcctcc       540
ggcctgtact ccctgagctc cgtggtgacc gtcccttcca gctccctggg caccaagacc       600
tatacctgta acgtggacca caagccctcc aataccaagg tggataagcg ggtcgagtcc       660
aagtacggac cccttgccc tccttgtcct gctcctgaat tcctcggcgg acctagcgtc       720
tttctcttcc cccccaagcc caaggatacc ctgatgatct ccaggacccc cgaggtgaca       780
tgcgtcgtgg tcgatgtgtc ccaggaggat cctgaagtgc agttcaactg gtacgtggac       840
ggcgtcgaag tgcataacgc caagaccaag cccagggagg agcagttcaa ctccacctat       900
cgggtggtga gcgtgctgac cgtgctgcat caggactggc tcaacggcaa agagtacaag       960
tgcaaggtct ccaacaaggg actcccctcc agcatcgaga gaccattag caaggccaaa       1020 ggccaaccca gggagcctca ggtatatacg ctgcccccca gccaggagga gatgaccaaa      1080
aaccaggtca gcctcacctg tctggtcaag ggcttctacc ctagcgacat tgctgtcgag      1140
tgggagagca acggccagcc cgagaacaac tataaaacca ccccccctgt cctggactcc      1200
gacggatcct tcttcctgta ctccaggctg acagtcgaca agtcccggtg gcaagaggga      1260
aacgtcttct cctgctccgt gatgcacgaa gctctccaca accactacac ccagaagagc      1320
ctcagcctgt ccctgggcaa atgatga                                         1347

<210> SEQ ID NO 28
<211> LENGTH: 1347
<212> TYPE: DNA
<213> ORGANISM: artificial sequence
<220> FEATURE:
<223> OTHER INFORMATION: HC of xd-16 D S228P IgG4

<400> SEQUENCE: 28
```

```
caggtgcagc tggtgcagtc tggggctgag gtgaagaagc ctgggtcctc ggtgaaggtc      60
tcctgcaagg cttctggagg caccttcagc agcactgcta tcagctgggt gcgacaggcc     120
cctggacaag ggcttgagtg gatgggaggg atctggccta gttttgatac agcaaactac     180
gcacagaagt tccggggcag agtcacgatt accgcggacg aatccacgag cacagcctac     240
atggagctga gcagcctgag atctgaggac acggcggtgt actactgcgc aagagccgag     300
tacagtagca caggaacctt tgattactgg ggacagggta cattggtcac cgtctcctca     360
gcttccacaa aggcccccag cgtgtttccc ctggcccctt gtagcaggtc cacctccgaa     420
agcacagccg ctctgggctg cctggtcaag gattacttcc ccgagccgt gaccgtgtcc      480
tggaatagcg gcgctctcac atccggagtg cataccttc ctgccgtgct ccagtcctcc      540
ggcctgtact ccctgagctc cgtggtgacc gtcccttcca gctccctggg caccaagacc     600
tatacctgta acgtggacca caagccctcc aataccaagg tggataagcg ggtcgagtcc     660
aagtacggac ccccttgccc tccttgtcct gctcctgaat tcctcggcgg acctagcgtc     720
tttctcttcc cccccaagcc caaggatacc ctgatgatct ccaggacccc cgaggtgaca     780
tgcgtcgtgg tcgatgtgtc caggaggat cctgaagtgc agttcaactg gtacgtggac     840
ggcgtcgaag tgcataacgc caagaccaag cccaggagg agcagttcaa ctccaccat      900
cgggtggtga gcgtgctgac cgtgctgcat caggactggc tcaacggcaa agagtacaag     960
tgcaaggtct ccaacaaggg actcccctcc agcatcgaga agaccattag caaggccaaa    1020
ggccaaccca gggagcctca ggtatatacg ctgccccca gccaggagga gatgaccaaa     1080
aaccaggtca gcctcacctg tctggtcaag ggcttctacc ctagcgacat tgctgtcgag    1140
tgggagagca cggccagcc cgagaacaac tataaaacca ccccccctgt cctggactcc    1200
gacggatcct tcttcctgta ctccaggctg acagtcgaca gtcccggtg caagaggga     1260
aacgtcttct cctgctccgt gatgcacgaa gctctccaca accactacac ccagaagagc    1320
ctcagcctgt ccctgggcaa atgatga                                       1347
```

<210> SEQ ID NO 29
<211> LENGTH: 1347
<212> TYPE: DNA
<213> ORGANISM: artificial sequence
<220> FEATURE:
<223> OTHER INFORMATION: HC of xd-16 E S228P IgG4

<400> SEQUENCE: 29

```
caggtgcagc tggtgcagtc tggggctgag gtgaagaagc ctgggtcctc ggtgaaggtc      60
tcctgcaagg cttctggagg caccttcagc agcactgcta tcagctgggt gcgacaggcc     120
cctggacaag ggcttgagtg gatgggaggg atctggccta gttttggtac agcaaactac     180
gcacggaagt tccagggcag agtcacgatt accgcggacg aatccacgag cacagcctac     240
atggagctga gcagcctgag atctgaggac acggcggtgt actactgcgc aagagccgag     300
tacagtagca caggaatctt tgattactgg ggacagggta cattggtcac cgtctcctca     360
gcttccacaa aggcccccag cgtgtttccc ctggcccctt gtagcaggtc cacctccgaa     420
agcacagccg ctctgggctg cctggtcaag gattacttcc ccgagccgt gaccgtgtcc      480
tggaatagcg gcgctctcac atccggagtg cataccttc ctgccgtgct ccagtcctcc      540
ggcctgtact ccctgagctc cgtggtgacc gtcccttcca gctccctggg caccaagacc     600
tatacctgta acgtggacca caagccctcc aataccaagg tggataagcg ggtcgagtcc     660
aagtacggac ccccttgccc tccttgtcct gctcctgaat tcctcggcgg acctagcgtc     720
```

```
tttctcttcc cccccaagcc caaggatacc ctgatgatct ccaggacccc cgaggtgaca      780
tgcgtcgtgg tcgatgtgtc ccaggaggat cctgaagtgc agttcaactg gtacgtggac      840
ggcgtcgaag tgcataacgc caagaccaag cccagggagg agcagttcaa ctccacctat      900
cgggtggtga gcgtgctgac cgtgctgcat caggactggc tcaacggcaa agagtacaag      960
tgcaaggtct ccaacaaggg actcccctcc agcatcgaga agaccattag caaggccaaa     1020
ggccaaccca gggagcctca ggtatatacg ctgcccccca gccaggagga gatgaccaaa     1080
aaccaggtca gcctcacctg tctggtcaag ggcttctacc ctagcgacat tgctgtcgag     1140
tgggagagca acggccagcc cgagaacaac tataaaacca ccccccctgt cctggactcc     1200
gacggatcct tcttcctgta ctccaggctg acagtcgaca gtcccggtg gcaagaggga      1260 aacgtcttct cctgctccgt gatgcacgaa gctctccaca accactacac ccagaagagc     1320
ctcagcctgt ccctgggcaa atgatga                                          1347

<210> SEQ ID NO 30
<211> LENGTH: 648
<212> TYPE: DNA
<213> ORGANISM: artificial sequence
<220> FEATURE:
<223> OTHER INFORMATION: LC of xd-16 A, xd-16 B, xd-16 C, xd-16 D, and
      xd-16 E

<400> SEQUENCE: 30
gacatccaga tgacccagtc tccatcttcc gtgtctgcat ctgtaggaga cagagtcacc       60
atcacttgtc gggcgagtca gggtattagc agctggttag cctggtatca gcagaaacca      120
gggaaagccc ctaagctcct gatctccgct gcatccagtt tgcaaagtgg ggtcccatca      180
aggttcagcg gcagtggatc tgggacagat ttcactctca ccatcagcag cctgcagcct      240
gaagattttg caacttatta ctgtcagcag gcaaatcacc tccctttcac ttttggcgga     300
gggaccaagg ttgagatcaa aggaccgtg gccgcccct ccgtgttcat ctttccccc        360 agcgacgagc agctgaagag cggcaccgcc tccgtggtgt gcctgctgaa caacttctat      420
ccccgggagg ccaaggtgca gtggaaggtc gacaatgccc tgcagagcgg caactcccag      480
gagagcgtga ccgagcagga cagcaaggac tccacctact ccctgagctc caccctgaca      540
ctgtccaagg ccgactacga gaagcacaag gtgtacgcct gcgaggtgac acaccagggc      600
ctgagctccc ccgtgaccaa gtccttcaac aggggcgagt gctgatga                  648
```

PD-1 ANTIBODIES

TECHNICAL FIELD

The present invention relates to the field of medicine. More particularly, the present invention relates to antibodies that bind human programmed cell death 1 (PD-1), and may be useful for treating cancer alone and in combination with chemotherapy and other cancer therapeutics.

BACKGROUND

Tumor cells escape detection and elimination by the immune system through multiple mechanisms. Immune checkpoint pathways are used in self-tolerance maintenance and activated T cell control, but cancer cells can use the pathways to prevent destruction. The PD-1/human programmed cell death 1 ligand 1 (PD-L1) pathway is one such immune checkpoint. Human PD-1 is found on T cells, and the binding of PD-L1 and human programmed cell death 1 ligand 2 (PD-L2) to PD-1 inhibits T cell proliferation and cytokine production. Tumor cell production of PD-L1 and PD-L2 can therefore allow escape from T cell surveillance.

A fully human IgG4 (S228P) antibody against human PD-1, nivolumab, has been shown to inhibit the binding of PD-1 to PD-L1 and PD-L2, and has been tested in various clinical trials. (Wang et al., Cancer Immunol Res (2014) 2(9): 846). A humanized IgG4 (S228P) antibody against PD-1, pembrolizumab (formerly lambrolizumab), has been shown to inhibit the binding of PD-1 to PD-L1 and PD-L2, and has been tested in various clinical trials. (WO2008156712 and Hamid et al., N Engl J Med (2013) 369:2).

There remains a need to provide alternative antibodies that bind and neutralize human PD-1 interaction with PD-L1 and PD-L2. In particular, there remains a need to provide antibodies that bind human PD-1 with high affinity. Also, there remains a need to provide antibodies that more effectively block the human PD-1 interaction with PD-L1 and PD-L2.

SUMMARY OF THE INVENTION

The first aspect of the present invention provides an antibody that binds human PD-1 (SEQ ID NO: 1), comprising a light chain (LC) and a heavy chain (HC), wherein the light chain comprises light chain complementarity determining regions LCDR1, LCDR2, and LCDR3 consisting of the amino acid sequences RASQGISSWLA (SEQ ID NO: 1.0), SAASSLQS (SEQ ID NO: 11), and QQANHLPFT (SEQ ID NO: 12), respectively, and the heavy chain comprises heavy chain complementarity determining regions HCDR1, HCDR2, and HCDR3, wherein HCDR1 consists of the amino acid sequences as set forth by KASGGTFSSTAIS (SEQ ID NO: 2 (for HCDR1 of xd-16 A, xd-16 B, xd-16 C, xd-16 D, and/or xd-16 E));

HCDR2 consists of the amino acid sequences as set forth by

GIWPSFGTANYAQKFQG (SEQ ID NO: 3 (for HCDR2 of xd-16 A)),
GIWPSFGTASYAQKFQG (SEQ ID NO: 4 (for HCDR2 of xd-16 B)),
GIWPSFGTASYAQKFRG (SEQ ID NO: 5 (for HCDR2 of xd-16 C)),
GIWPSFDTANYAQKFRG (SEQ ID NO: 6 (for HCDR2 of xd-16 D)), or
GIWPSFGTANYARKFQG (SEQ ID NO: 7 (for HCDR2 of xd-16 E)); and HCDR3 consists of the amino acid sequences as set forth by ARAEYSSTGTFDY (SEQ ID NO: 8 (for HCDR3 of xd-16 A, xd-16 C, and/or xd-16 D)), or ARAEYSSTGIFDY (SEQ ID NO: 9 (for HCDR3 of xd-16 B, and/or xd-16 E)).

Certain antibodies of the present invention bind human PD-1 with a high affinity that is greater than nivolumab and pembrolizumab under certain conditions. Furthermore, certain antibodies of the present invention mediate preferential enhanced alloreactivity compared to nivolumab and pembrolizumab in an in vivo model.

In an embodiment, the present invention provides an antibody, wherein LCDR1, LCDR2, and LCDR3 consist of the amino acid sequences RASQGISSWLA (SEQ ID NO: 10), SAASSLQS (SEQ ID NO: 11), and QQANHLPFT (SEQ ID NO: 12), respectively, and wherein HCDR1, HCDR2, and HCDR3 consist of the amino acid sequences KASGGTFSSTAIS (SEQ ID NO: 2), GIWPSFGTANYAQKFQG (SEQ ID NO: 3), and ARAEYSSTGTFDY (SEQ ID NO: 8), respectively.

In a further embodiment, the present invention provides an antibody, wherein LCDR1, LCDR2, and LCDR3 consist of the amino acid sequences RASQGISSWLA (SEQ ID NO: 10), SAASSLQS (SEQ ID NO: 11), and QQANHLPFT (SEQ ID NO: 12), respectively, and wherein HCDR1, HCDR2, and HCDR3 consist of the amino acid sequences KASGGTFSSTAIS (SEQ ID NO: 2), GIWPSFGTASYAQKFQG (SEQ ID NO: 4), and ARAEYSSTGIFDY (SEQ ID NO: 9), respectively.

In a further embodiment, the present invention provides an antibody, wherein LCDR1, LCDR2, and LCDR3 consist of the amino acid sequences RASQGISSWLA (SEQ ID NO: 10), SAASSLQS (SEQ ID NO: 11), and QQANHLPFT (SEQ ID NO: 12), respectively, and wherein HCDR1, HCDR2, and HCDR3 consist of the amino acid sequences KASGGTFSSTAIS (SEQ ID NO: 2), GIWPSFGTASYAQKFRG (SEQ ID NO: 5), and ARAEYSSTGTFDY (SEQ ID NO: 8), respectively.

In a further embodiment, the present invention provides an antibody, wherein LCDR1, LCDR2, and LCDR3 consist of the amino acid sequences RASQGISSWLA (SEQ ID NO: 10), SAASSLQS (SEQ ID NO: 11), and QQANHLPFT (SEQ ID NO: 12), respectively, and wherein HCDR1, HCDR2, and HCDR3 consist of the amino acid sequences KASGGTFSSTAIS (SEQ ID NO: 2), GIWPSFDTANYAQKFRG (SEQ ID NO: 6), and ARAEYSSTGTFDY (SEQ ID NO: 8), respectively.

In a further embodiment, the present invention provides an antibody, wherein LCDR1, LCDR2, and LCDR3 consist of the amino acid sequences RASQGISSWLA (SEQ ID NO: 10), SAASSLQS (SEQ ID NO: 11), and QQANHLPFT (SEQ ID NO: 12), respectively, and wherein HCDR1, HCDR2, and HCDR3 consist of the amino acid sequences KASGGTFSSTAIS (SEQ ID NO: 2), GIWPSFGTANYARKFQG (SEQ ID NO: 7), and ARAEYSSTGIFDY (SEQ ID NO: 9), respectively.

In an embodiment, the present invention provides an antibody, comprising 1 or 2 light chain (s) (LC) and 1 or 2 heavy chain (s) (HC), wherein each of the light chain comprises a light chain variable region (LCVR) and each of the heavy chain comprises a heavy chain variable region (HCVR), wherein the LCVR has the amino acid sequence given in SEQ ID NO: 18, and the HCVR has the amino acid sequence as set forth by SEQ ID NO: 13, SEQ ID NO: 14, SEQ ID NO: 15, SEQ ID NO: 16, or SEQ ID NO: 17.

In a further embodiment, the present invention provides an antibody, wherein the LCVR has the amino acid sequence as set forth by SEQ ID NO: 18, and the HCVR has the amino acid sequence as set forth by SEQ ID NO: 13.

In a further embodiment, the present invention provides an antibody, wherein the LCVR has the amino acid sequence as set forth by SEQ ID NO: 18, and the HCVR has the amino acid sequence as set forth by SEQ ID NO: 14.

In a further embodiment, the present invention provides an antibody, wherein the LCVR has the amino acid sequence as set forth by SEQ ID NO: 18, and the HCVR has the amino acid sequence as set forth by SEQ ID NO: 15.

In a further embodiment, the present invention provides an antibody, wherein the LCVR has the amino acid sequence as set forth by SEQ ID NO: 18, and the HCVR has the amino acid sequence as set forth by SEQ ID NO: 16.

In a further embodiment, the present invention provides an antibody, wherein the LCVR has the amino acid sequence as set forth by SEQ ID NO: 18, and the HCVR has the amino acid sequence as set forth by SEQ ID NO: 17.

In an embodiment, the present invention provides an antibody, wherein the LC has the amino acid sequence as set forth by SEQ ID NO: 24, and the HC has the amino acid sequence as set forth by SEQ ID NO: 19, SEQ ID NO: 20, SEQ ID NO: 21, SEQ ID NO: 22, or SEQ ID NO: 23.

In a further embodiment, the present invention provides an antibody, wherein the LC has the amino acid sequence as set forth by SEQ ID NO: 24, and the HC has the amino acid sequence as set forth by SEQ ID NO: 19.

In a further embodiment, the present invention provides an antibody, wherein the LC has the amino acid sequence as set forth by SEQ ID NO: 24, and the HC has the amino acid sequence as set forth by SEQ ID NO: 20.

In a further embodiment, the present invention provides an antibody, wherein the LC has the amino acid sequence as set forth by SEQ ID NO: 24, and the HC has the amino acid sequence as set forth by SEQ ID NO: 21.

In a further embodiment, the present invention provides an antibody, wherein the LC has the amino acid sequence as set forth by SEQ ID NO: 24, and the HC has the amino acid sequence as set forth by SEQ ID NO: 22.

In a further embodiment, the present invention provides an antibody, wherein the LC has the amino acid sequence as set forth by SEQ ID NO: 24, and the HC has the amino acid sequence as set forth by SEQ ID NO: 23.

In an embodiment, the present invention provides an antibody, comprising two light chains and two heavy chains, wherein each light chain has the amino acid sequence as set forth by SEQ ID NO: 24, and each heavy chain has the amino acid sequence as set forth by SEQ ID NO: 19, SEQ ID NO: 20, SEQ ID NO: 21, SEQ ID NO: 22, or SEQ ID NO: 23.

In a further embodiment, the present invention provides an antibody, wherein each light chain has the amino acid sequence as set forth by SEQ ID NO: 24, and each heavy chain has the amino acid sequence as set forth by SEQ ID NO: 19.

In a further embodiment, the present invention provides an antibody, wherein each light chain has the amino acid sequence as set forth by SEQ ID NO: 24, and each heavy chain has the amino acid sequence as set forth by SEQ ID NO: 20.

In a further embodiment, the present invention provides an antibody, wherein each light chain has the amino acid sequence as set forth by SEQ ID NO: 24, and each heavy chain has the amino acid sequence as set forth by SEQ ID NO: 21.

In a further embodiment, the present invention provides an antibody, wherein each light chain has the amino acid sequence as set forth by SEQ ID NO: 24, and each heavy chain has the amino acid sequence as set forth by SEQ ID NO: 22.

In a further embodiment, the present invention provides an antibody, wherein each light chain has the amino acid sequence as set forth by SEQ ID NO: 24, and each heavy chain has the amino acid sequence as set forth by SEQ ID NO: 23.

In an embodiment, the present invention provides an antibody, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In an embodiment, the present invention provides an antibody, wherein the antibody is glycosylated.

In an embodiment, the present invention provides an antibody that binds human PD-1 (SEQ ID NO: 1), comprising a light chain (LC) and a heavy chain (HC), wherein the light chain comprises a light chain variable region (LCVR) and the heavy chain comprises a heavy chain variable region (HCVR), wherein the LCVR has the amino acid sequence as set forth by SEQ ID NO: 18, and the HCVR has the amino acid sequence as set forth by SEQ ID NO: 13, SEQ ID NO: 14, SEQ ID NO: 15, SEQ ID NO: 16, or SEQ ID NO: 17.

In a further embodiment, the present invention provides an antibody that binds human PD-1 (SEQ ID NO: 1), wherein the LCVR has the amino acid sequence as set forth by SEQ ID NO: 18, and the HCVR has the amino acid sequence as set forth by SEQ ID NO: 13. In a further embodiment, the present invention provides an antibody that binds human PD-1 (SEQ ID NO: 1), wherein the LCVR has the amino acid sequence as set forth by SEQ ID NO: 18, and the HCVR has the amino acid sequence as set forth by SEQ ID NO: 14. In a further embodiment, the present invention provides an antibody that binds human PD-1 (SEQ ID NO: 1), wherein the LCVR has the amino acid sequence as set forth by SEQ ID NO: 18, and the HCVR has the amino acid sequence as set forth by SEQ ID NO: 15. In a further embodiment, the present invention provides an antibody that binds human PD-1 (SEQ ID NO: 1), wherein the LCVR has the amino acid sequence as set forth by SEQ ID NO: 18, and the HCVR has the amino acid sequence as set forth by SEQ ID NO: 16. In a further embodiment, the present invention provides an antibody that binds human PD-1 (SEQ ID NO: 1), wherein the LCVR has the amino acid sequence as set forth by SEQ ID NO: 18, and the HCVR has the amino acid sequence as set forth by SEQ ID NO: 17.

In an embodiment, the present invention provides an antibody that binds human PD-1 (SEQ ID NO: 1), wherein the LC has the amino acid sequence as set forth by SEQ ID NO: 24, and the HC has the amino acid sequence as set forth by SEQ ID NO: 19, SEQ ID NO: 20, SEQ ID NO: 21, SEQ ID NO: 22, or SEQ ID NO: 23.

In a further embodiment, the present invention provides an antibody that binds human PD-1 (SEQ ID NO: 1), wherein the LC has the amino acid sequence as set forth by SEQ ID NO: 24, and the HC has the amino acid sequence as set forth by SEQ ID NO: 19. In a further embodiment, the present invention provides an antibody that binds human PD-1 (SEQ ID NO: 1), wherein the LC has the amino acid sequence as set forth by SEQ ID NO: 24, and the HC has the amino acid sequence as set forth by SEQ ID NO: 20. In a further embodiment, the present invention provides an antibody that binds human PD-1 (SEQ ID NO: 1), wherein the LC has the amino acid sequence as set forth by SEQ ID NO: 24, and the HC has the amino acid sequence as set forth by SEQ ID NO: 21. In a further embodiment, the present invention provides an antibody that binds human PD-1 (SEQ ID NO: 1), wherein the LC has the amino acid sequence as set forth by SEQ ID NO: 24, and the HC has the amino acid sequence as set forth by SEQ ID NO: 22. In a further embodiment, the present invention provides an antibody that binds human PD-1 (SEQ ID NO: 1), wherein the LC has the amino acid sequence as set forth by SEQ ID NO: 24, and the HC has the amino acid sequence as set forth by SEQ ID NO: 23.

In an embodiment, the present invention provides an antibody that binds human PD-1 (SEQ ID NO: 1), comprising two light chains and two heavy chains, wherein each light chain has the amino acid sequence as set forth by SEQ ID NO: 24, and each heavy chain has the amino acid sequence as set forth by SEQ ID NO: 19, SEQ ID NO: 20, SEQ ID NO: 21, SEQ ID NO: 22, or SEQ ID NO: 23.

In a further embodiment, the present invention provides an antibody that binds human PD-1 (SEQ ID NO: 1), wherein each light chain has the amino acid sequence as set forth by SEQ ID NO: 24, and each heavy chain has the amino acid sequence as set forth by SEQ ID NO: 19. In a further embodiment, the present invention provides an antibody that binds human PD-1 (SEQ ID NO: 1), wherein each light chain has the amino acid sequence as set forth by SEQ ID NO: 24, and each heavy chain has the amino acid sequence as set forth by SEQ ID NO: 20. In a further embodiment, the present invention provides an antibody that binds human PD-1 (SEQ ID NO: 1), wherein each light chain has the amino acid sequence as set forth by SEQ ID NO: 24, and each heavy chain has the amino acid sequence as set forth by SEQ ID NO: 21. In a further embodiment, the present invention provides an antibody that binds human PD-1 (SEQ ID NO: 1), wherein each light chain has the amino acid sequence as set forth by SEQ ID NO: 24, and each heavy chain has the amino acid sequence as set forth by SEQ ID NO: 22. In a further embodiment, the present invention provides an antibody that binds human PD-1 (SEQ ID NO: 1), wherein each light chain has the amino acid sequence as set forth by SEQ ID NO: 24, and each heavy chain has the amino acid sequence as set forth by SEQ ID NO: 23. In an embodiment, the present invention provides an antibody that binds human PD-1 (SEQ ID NO: 1), wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In an embodiment, the present invention provides an antibody that binds human PD-1 (SEQ ID NO: 1), wherein the antibody is glycosylated.

The second aspect of the present invention provides a polynucleotide encoding any one of the above antibodies of the present invention, the fragments or the derivatives thereof.

In another preferred embodiment, the polynucleotide encoding HC of xd-16 A S228P IgG4 is as set forth by SEQ ID NO: 25.

In another preferred embodiment, the polynucleotide encoding HC of xd-16 B S228P IgG4 is as set forth by SEQ ID NO: 26.

In another preferred embodiment, the polynucleotide encoding HC of xd-16 C S228P IgG4 is as set forth by SEQ ID NO: 27.

In another preferred embodiment, the polynucleotide encoding HC of xd-16 D S228P IgG4 is as set forth by SEQ ID NO: 28.

In another preferred embodiment, the polynucleotide encoding HC of xd-16 E S228P IgG4 is as set forth by SEQ ID NO: 29.

In another preferred embodiment, the polynucleotide encoding LC of xd-16 A, xd-16 B, xd-16 C, xd-16 D, and xd-16 E is as set forth by SEQ ID NO: 30.

The third aspect of the present invention provides a vector comprising the polynucleotide of the third aspect.

The fourth aspect of the present invention provides a host cell comprising the vector of the third aspect or the genome of said cell is integrated with exogenous polynucleotide according to the second aspect.

In a preferred embodiment, said host cell is a mammalian cell, preferably, a CHO cell.

In an embodiment, the present invention provides a mammalian cellcomprising a DNA molecule comprising a polynucleotide sequence encoding a polypeptide having an amino acid sequence of SEQ ID NO: 24 and a polynucleotide sequence encoding a polypeptide having an amino acid sequence of SEQ ID NO: 19, wherein the cell is capable of expressing an antibody comprising a light chain having an amino acid sequence of SEQ ID NO: 24 and a heavy chain having an amino acid sequence of SEQ ID NO: 19.

In an embodiment, the present invention provides a mammalian cell, comprising a DNA molecule comprising a polynucleotide sequence encoding a polypeptide having an amino acid sequence of SEQ ID NO: 24 and a polynucleotide sequence encoding a polypeptide having an amino acid sequence of SEQ ID NO: 20, wherein the cell is capable of expressing an antibody comprising a light chain having an amino acid sequence of SEQ ID NO: 24 and a heavy chain having an amino acid sequence of SEQ ID NO: 20.

In an embodiment, the present invention provides a mammalian cell, comprising a DNA molecule comprising a polynucleotide sequence encoding a polypeptide having an amino acid sequence of SEQ ID NO: 24 and a polynucleotide sequence encoding a polypeptide having an amino acid sequence of SEQ ID NO: 21, wherein the cell is capable of expressing an antibody comprising a light chain having an amino acid sequence of SEQ ID NO: 24 and a heavy chain having an amino acid sequence of SEQ ID NO: 21.

In an embodiment, the present invention provides a mammalian cell, comprising a DNA molecule comprising a polynucleotide sequence encoding a polypeptide having an amino acid sequence of SEQ ID NO: 24 and a polynucleotide sequence encoding a polypeptide having an amino acid sequence of SEQ ID NO: 22, wherein the cell is capable of expressing an antibody comprising a light chain having an amino acid sequence of SEQ ID NO: 24 and a heavy chain having an amino acid sequence of SEQ ID NO: 22.

In an embodiment, the present invention provides a mammalian cell, comprising a DNA molecule comprising a polynucleotide sequence encoding a polypeptide having an amino acid sequence of SEQ ID NO: 24 and a polynucleotide sequence encoding a polypeptide having an amino acid sequence of SEQ ID NO: 23, wherein the cell is capable of expressing an antibody comprising a light chain having an amino acid sequence of SEQ ID NO: 24 and a heavy chain having an amino acid sequence of SEQ ID NO: 23.

The fifth aspect of the present invention, a process is provided for producing an antibody comprising a light chain having an amino acid sequence of SEQ ID NO: 24 and a heavy chain having an amino acid sequence of SEQ ID NO: 20, comprising cultivating the host cell of the fourth aspect under conditions such that the antibody is expressed, and recovering the expressed antibody In an embodiment, the present invention provides an antibody produced by a process of the present invention.

The sixth aspect of the present invention provides a pharmaceutical composition comprising an antibody of the present invention, and a pharmaceutical acceptable carrier.

The seventh aspect of the present invention provides a method of treating cancer comprising step of administering to a subject in need with an effective amount of an antibody of the present invention.

In a further embodiment, the method of treating cancer further comprises the step of administering to a subject in need with an effective amount of the antibody of the present invention, wherein the cancer is melanoma, lung cancer, head and neck cancer, colorectal cancer, pancreatic cancer, gastric cancer, kidney cancer, bladder cancer, prostate cancer, breast cancer, ovarian cancer, or liver cancer.

In a further embodiment, these methods comprise the administration of an effective amount of the antibody of the present invention in simultaneous, separate, or sequential combination with one or more anti-tumor agent(s), immuno-oncology agent(s), or the combination thereof.

In a preferred embodiment, said anti-tumor agents includes, but not limited to, ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), cetuximab, or the combination thereof.

In a further embodiment, said immuno-oncology agents includes, but not limited to, nivolumab, ipilimumab, pidilizumab, pembrolizumab, tremelimumab, urelumab, lirilumab, atezolizumab, durvalumab, or the combination thereof.

The eighth aspect of the present invention provides an antibody of the present invention for use in therapy.

The ninth aspect of the present invention provides an antibody of the present invention for use in the treatment of cancer.

In a further embodiment, the present invention provides an antibody of the present invention for use in the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, or liver cancer.

The tenth aspect of the present invention provide the antibody of any one of the aspect of the present invention in simultaneous, separate, or sequential combination with one or more anti-tumor agents, immuno-oncology agents, and combination thereof for combined use in treatment of cancer.

In a preferred embodiment, said anti-tumor agents include, but not limited to, ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), cetuximab, or the combination thereof.

In a further embodiment, said immuno-oncology agents include, but not limited to, nivolumab, ipilimumab, pidilizumab, pembrolizumab, tremelimumab, urelumab, lirilumab, atezolizumab, durvalumab, or the combination thereof.

The eleventh aspect of the present invention provides the use of an antibody of the present invention for preparing a pharmaceutical composition for treatment of cancer.

In a further embodiment, the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

In a further embodiment, said pharmaceutical composition further comprises one or more of anti-tumor agents and/or immuno-oncology agents.

In a further embodiment, said pharmaceutical composition is administered to a subject in need in simultaneous, separate, or sequential combination with one or more of anti-tumor agents and/or immuno-oncology agents.

In a preferred embodiment, said anti-tumor agents include, but not limited to, ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), cetuximab, or the combination thereof.

In a further embodiment, said immuno-oncology agents include, but not limited to, nivolumab, ipilimumab, pidilizumab, pembrolizumab, tremelimumab, urelumab, lirilumab, atezolizumab, durvalumab, or the combination thereof.

It should be understood that in the present invention, the technical features specifically described above and below (such as in the Examples) can be combined with each other, thereby constituting a new or preferred technical solution which needs not be described one by one.

DETAILED DESCRIPTION

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

An antibody of the present invention is designed to have engineered CDRs and have some portions of the antibody (all or parts of the frameworks, hinge regions, and constant regions) to be of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. An antibody of the present invention may comprise framework, hinge, or constant regions derived from a fully human framework, hinge, or constant region containing one or more amino acid substitutions, deletions, or additions therein. Further, an antibody of the present invention is preferably substantially non-immunogenic in humans.

The antibody of the present invention is an IgG type antibody and has four amino acid chains (two "heavy"

chains and two "light" chains) that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the antibody of the present invention contains an Fc portion which is derived from human $IgG_4$ Fc region because of a reduced ability to engage Fc receptor-mediated inflammatory mechanisms or to activate complement resulting in reduced effector function.

The S228P mutation is a hinge mutation that prevents half-antibody formation (phenomenon of dynamic exchange of half-molecules in $IgG_4$ antibodies). The F234A and L235A mutations further reduce effector function of the already low human $IgG_4$ isotype.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987), Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, the North CDR definitions are used.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy,* $19^{th}$ ed. (1995), A. Gennaro et al., Mack Publishing Co.) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human PD-1 is intended to mean, unless indicated otherwise, a $K_D$ of less than about 1×10-9 M, preferably, less than about 2×10-10 M as determined by common methods known in the art, including by use of a surface plasmon resonance (SPR) biosensor at 37° C. essentially as described herein.

For the purposes of the present disclosure, the term "high affinity" refers to a $K_D$ of less than about 150 pM for human PD-1. The $K_D$ values are established by binding kinetics as described in "Binding kinetics and affinity" in the Assays section.

The present invention further provides a pharmaceutical composition comprising the polypeptide of the present invention or the agonist thereof with safe and effective amounts and pharmaceutically acceptable carrier (s) or excipient (s). These carriers include (but are not limited to): saline, buffer solution, glucose, water, glycerol, ethanol, or the combination thereof. The pharmaceutical preparation should match the administration mode. The pharmaceutical composition of the present invention can be prepared into the form of injection, such as being prepared with saline or aqueous solution containing glucose or other auxiliaries by conventional methods. Pharmaceutical compositions, such as tablets and capsules can be prepared with conventional methods. Pharmaceutical compositions such as injections, solution, tablets and capsules may be preferably produced in sterile conditions. The administration amount of the active ingredients is a therapeutically effective amount, for example, about 1 µg/kg (body weight)-5 mg/kg (body weight) per day. Moreover, the polypeptide of the present invention can be further used with other therapeutical agents.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecular Cloning: A Laboratory Manual, New York: Cold Spring Harbor Laboratory Press, 2012, or as instructed by the manufacturers. Unless otherwise specified, the percentage and portion refer to weight percentage and weight portion.

Major Advantages of the Present Invention:

xd-16 B, xd-16 C, xd-16 D and xd-16 E, binds human PD-1 with an affinity higher than pembrolizumab and nivolumab in both monovalent and avid binding modes. Antibody xd-16 B at each concentration increased IL-2 of IFN-γ comparable or better than to nivolumab and pembrolizumab in immune cell activation assays.

EXAMPLES

Example 1: Antibody Expression and Purification

The polypeptides of the variable regions of the heavy chain and light chain, the complete heavy chain and light chain amino acid sequences of Antibody A—Antibody I, and the nucleotide sequences encoding the same, are listed below in the section entitled "Amino Acid and Nucleotide Sequences." In addition, the SEQ ID NOs for the light chain, heavy chain, light chain variable region, and heavy chain variable region of Antibody A—Antibody I are shown in Table 1.

The antibodies of the present invention, including, but not limited to, Antibody A—Antibody I can be made and purified essentially as follows. An appropriate host cell, such as HEK 293 or CHO, can be either transiently or stably transfected with an expression system for secreting antibodies using an optimal predetermined HC:LC vector ratio (such as 1:3 or 1:2) or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at −70° C. or may be lyophilized.

TABLE 1

| | SEQ ID NOs | | | | |
|---|---|---|---|---|---|
| | Antibody A S228P IgG4 (xd-16 A) | Antibody B S228P IgG4 (xd-16 B) | Antibody C S228P IgG4 (xd-16 C) | Antibody D S228P IgG4 (xd-16 D) | Antibody E S228P IgG4 (xd-16 E) |
| HCVR | 13 | 14 | 15 | 16 | 17 |
| LCVR | 18 | 18 | 18 | 18 | 18 |
| Heavy chain | 19 | 20 | 21 | 22 | 23 |
| Light chain | 24 | 24 | 24 | 24 | 24 |

Assays

Binding Kinetics and Affinity

The kinetics and equilibrium dissociation constant ($K_D$) for human PD-1 is determined for antibodies of the present invention using MSD, surface plasmon resonance (Biacore), bio-light interferometry (ForteBio) assay methods.

As used herein, nivolumab is a human IgG4 PD-1 antibody transiently expressed in 293 HEK cells that utilizes the heavy chain and light chain sequences from Proposed INN: List 107 (CAS #946414-94-4). As used herein, pembrolizumab is a human IgG4 PD-1 antibody transiently expressed in 293 HEK cells that utilizes the heavy chain and light chain sequences from Proposed INN: List 72.

MSD Assay

Equilibrium affinity measurements are performed as previously described (Estep, P., et al., MAbs, 2013.5 (2): p. 270-8). Solution equilibrium titrations (SET) are performed in PBS+0.1% IgG-Free BSA (PBSF) where antigen (b-PD-1 monomer) is held constant at 10-100 pM and is incubated with 3- to 5-fold serial dilutions of Fab or mAbs starting at 5-100 nM (experimental condition is sample dependent). Antibodies diluted at 20 nM in PBS are coated onto standard bind MSD-ECL plates overnight at 4° C. or at room temperature for 30 min. Plates are blocked with BSA for 30 min whilst shaking at 700 rpm. Plates are then washed 3× with wash buffer (PBSF+0.05% Tween 20). SET samples are applied and incubated on the plates for 150 s with shaking at 700 rpm followed by one wash. Antigen captured on a plate is detected with 250 ng/mL sulfotag-labeled streptavidin in PBSF by incubation on the plate for 3 min. The plates are washed three times with wash buffer and are then read on the MSD Sector Imager 2400 instrument using 1× Read Buffer T with surfactant. The percent free antigen is plotted as a function of titrated antibody in Prism and fit to a quadratic equation to extract the KD. To improve throughput, liquid handling robots are used throughout MSD-SET experiments, including for SET sample preparation.

In experiments performed essentially as described in this assay, xd-16 B, xd-16 C, xd-16 D and xd-16 E, in an IgG1 format and expressed in yeast, bind human PD-1 with a $K_D$ of 45 pM. 50 pM. 93 pM and 150 pM respectively. Pembrolizumab and nivolumab bind PD-1 with a $K_D$ of 130 pM and 640 pM respectively. Avidity measurements for xd-16 B, xd-16 C, xd-16 D and xd-16 E, result in a $K_D$ of approximately 0.9 pM, 2.5 pM, 1.3 pM and 0.9 pM respectively. Pembrolizumab and nivolumab bind human PD-1 with a $K_D$ of approximately 3 pM and 5 pM respectively.

TABLE 2

Binding by MSD of antibodies of the invention in IgG1 format

| Name | Monovalent KD (pM) against human PD-1 | Avid KD (pM) against human PD-1 |
|---|---|---|
| xd-16 B | 45 | ~0.9 |
| xd-16 C | 50 | 2.5 |
| xd-16 D | 93 | 1.3 |
| xd-16 E | 150 | ~0.9 |
| Pembrolizumab | 130 | ~3 |
| Nivolumab | 640 | ~5 |

Bio-Light Interferometry

ForteBio affinity measurements were performed generally as previously described (Estep, P., et al., *High throughput solution-based measurement of antibody-antigen affinity and epitope binning.* MAbs, 2013. 5(2): p. 270-8.). Briefly, ForteBio affinity measurements were performed by loading IgGs online onto AHQ sensors. Sensors were equilibrated off-line in assay buffer for 30 min and then monitored on-line for 60 seconds for baseline establishment. Sensors with loaded IgGs were exposed to 100 nM antigen for 5 min, afterwards they were transferred to assay buffer for 5 min for off-rate measurement. Kinetics was analyzed using the 1:1 binding model.

In experiments performed essentially as described in this assay, xd-16 B, xd-16 C, xd-16 D and xd-16 E, in a Fab format produced from IgG1 expressed in yeast, bind human PD-1_Fc with a $K_D$ approximately twofold to threefold lower than nivolumab and pembrolizumab when PD-1_Fc was on the sensor tip. When the antibody was on the sensor tip, xd-16 B, xd-16 C, xd-16 D and xd-16 E, in an IgG1 format and expressed in yeast, bind human PD-1_His with a $K_D$ approximately threefold to fourfold lower than nivolumab and pembrolizumab. xd-16 B, xd-16 C, xd-16 D and xd-16 E, in a Fab format produced from IgG1 expressed in yeast, bind cynoPD-1_Fc with a similar $K_D$ to nivolumab and pembrolizumab.

TABLE 3

Binding by Bio-light interferometry of antibodies of the invention in IgG1 format

|  | Monovalent $K_D$ (M) Fab in solution, hPD-1_Fc on sensor tip | Monovalent $K_D$ (M) hPD-1_HIS in solution, IgG on sensor tip | Monovalent $K_D$ (M) Fab in solution, cynoPD-1_Fc on sensor tip |
|---|---|---|---|
| xd-16 B | 6.30E−10 | 4.20E−10 | 7.80E−10 |
| xd-16 C | 5.70E−10 | 3.80E−10 | 7.30E−10 |
| xd-16 D | 9.90E−10 | 6.50E−10 | 1.20E−09 |
| xd-16 E | 8.60E−10 | 5.60E−10 | 1.00E−09 |
| Pembrolizumab | 2.00E−09 | 2.00E−09 | 4.70E−10 |
| Nivolumab | 1.70E−09 | 4.10E−09 | 1.20E−09 |

Binding to Human PD-1 on CHO Cells

The binding of an antibody of the present invention to human PD-1 may be measured in a flow cytometry assay.

CHO cells (0.2×10⁶) are incubated with the experimental antibody from 200 nM titrated 19× by a factor of 2 to the lowest concentration of 3.185 pM for 30 min in PBS 1% BSA on ice. Cells are then washed 3×, and are incubated with a secondary antibody (PE-labelled, at final concentration of 5 μg/ml) in PBS 1% BSA for 30 min on ice (protected from light). Cells are washed 3× and analyzed via flow cytometry. Flow cytometry is performed on an Accuri C6 system (BD Biosciences) and MFIs are calculated on the C6 software. EC50s are calculated on Graphpad software.

In experiments performed essentially as described in this assay, xd-16 B (IgG4 S228P) binds PD-1 in a dose-dependent manner, with an EC50 value (n=1) of 1.461 nM, xd-16 D (IgG4 S228P) binds PD-1 in a dose-dependent manner, with an EC50 value (n=1) of 1.471 nM, nivolumab (IgG4 S228P) binds PD-1 in a dose-dependent manner, with an EC50 value (n=1) of 1.311 nM. In experiments performed essentially as described in this assay, xd-16 B and xd-16 D binds with a similar EC50 to human PD-1 as nivolumab under these conditions.

TABLE 4

Binding to human PD-1 on CHO cells

|  | xd-16 B IgG4 | xd-16 D IgG4 | Nivolumab IgG4 |
|---|---|---|---|
| Binding to PD-1 (EC50 nM) | 1.461 | 1.471 | 1.311 |

Blocking of Human PD-1 to PD-L1 and PD-L2 in CHO Cells.

The ability of an antibody of the present invention to block binding of human PD-1 to PD-L1 and PD-L2 may be measured by flow cytometry.

CHO cells 0.2×10⁶ are incubated with the experimental antibody (100 nM) for 30 min in PBS 1% BSA on ice. Cells are then washed 3×, and are incubated with PD-L2 linked with NHS-Fluorescein (Promega) in PBS 1% BSA for 30 min on ice (protected from light). Cells are washed 3× and analyzed via flow cytometry. Flow cytometry is performed on an Accuri C6 system (BD Biosciences) and MFIs are calculated on the C6 software. EC50 s are calculated on Graphpad software.

In experiments performed essentially as described in this assay, xd-16 B, xd-16 C, xd-16 D and xd-16 E (IgG1 format expressed in yeast) blocked human PD-L2-F1TC binding, resulting in an MFI of 26,445.9, 26,524.8, 39,983.1 and 40,867.9 respectively as compared to control IgG which resulted in an MFI of 182,959.1. Pembrolizumab and nivolumab resulted in MFI's of 46,245.9 and 54,509.8 respectively.

TABLE 5

Blocking of human PD-1 on CHO cells

| Test Sample | MFI (PD-L2-FITC) |
|---|---|
| Cells only | 33,449.7 |
| No IgG | 199,716.0 |
| IgG Control | 182,959.1 |
| Nivolumab | 54,509.8 |
| Pembrolizumab | 46,245.9 |
| xd-16 B | 26,445.9 |
| xd-16 C | 26,524.8 |
| xd-16 D | 39,983.1 |
| xd-16 E | 40,867.9 |

Mixed Lymphocyte Reaction

The blocking of PD-1 signals by antibodies of the present invention may be evaluated by measuring the release of inhibitory signals during T cell activation.

$2 \times 10^6$ PBHC are plated per well in a 6 well tissue culture plate or T25 tissue culture flask in complete T cell media. Cells are incubated for 2-3 hours, to allow for adherence of monocytes. If adherence is insufficient, serum free media is used. Unattached cells are removed by gently swirling the flask with fresh media 3×.

Immature myeloid DCs are generated by culturing monocytes ($1 \times 10^6$ cells/ml) from PBHC in X-VIVO 15 media containing 1% AB serum, 10 mM HEPES, 50 µM β-Me, IL-4 (1000 U/ml) and GM-CSF (1000 U/ml), or 25-50 ng/ml of each. After 2 days fresh medium supplemented with IL-4 and GM-CSF is added. On Day 5, cells are either frozen or maturation is induced by adding a stimulation cocktail containing rTNFa (1000 U/ml), IL-1b (5 ng/ml), IL-6 (10 ng/ml) and 1 µM $PGE_2$ for 2 days at a cell density of $3 \times 10^5$ cells/ml.

T cell Isolation is performed as per manufacturer's instructions in the Untouched CD4+ T cell isolation kit (Invitrogen). A magnet fitted with a 1.5 ml tube rack is used to remove unwanted magnetic beads (QIAGEN).

100,000-200,000 isolated T cells are mixed with 10,000-20,000 allogeneic moDCs in a total volume of 200 µl in 96-round bottom tissue culture plates for 4-5 days at 37° C. T cells are stimulated using anti-CD3/CD28 DynaBeads at a ratio of 3:1 (cells:beads) as a positive control; beads are prepared as per the manufacturer's instructions. Test antibodies are added at the beginning of the MLR and incubated throughout the culture period.

Detection of IL-2 and IFN-γ is carried out as per manufacturer's instructions (eBioscience). OD measurements are determined on a Multiskan FC system (Thermo).

In experiments performed essentially as described in this assay, Antibody xd-16 B at each concentration increased IL-2 of IFN-γ comparable to nivolumab and pembrolizumab.

TABLE 6

IL-2 secretion fold change vs. IgG control

| | Concentrations of IgG | | | | |
|---|---|---|---|---|---|
| | 100 nM | 10 nM | 1 nM | 0.1 nM | 0.01 nM |
| Pembrolizumab | 2.03114 | 2.49216 | 2.04189 | 1.47268 | 1.05915 |
| Nivolumab | 2.37395 | 2.44395 | 1.71526 | 1.26004 | 1.0918 |
| xd-16 B | 2.3661 | 2.38817 | 2.18347 | 1.45926 | 1.14941 |

TABLE 7

IFNg secretion fold change vs. IgG control

| | Concentrations of IgG | | | | |
|---|---|---|---|---|---|
| | 100 nM | 10 nM | 1 nM | 0.1 nM | 0.01 nM |
| Pembrolizumab | 1.78083 | 1.771 | 1.75723 | 1.98907 | 1.02989 |
| Nivolumab | 1.97395 | 1.877 | 1.57676 | 1.52809 | 0.83909 |
| xd-16 B | 1.89709 | 2.1678 | 2.14839 | 1.58718 | 1.08886 |

All references mentioned in the present invention are incorporated herein by reference, as each of them is individually cited herein by reference. Further, it should be understood that, after reading the above contents, the skilled person can make various modifications or changes to the present invention. All these equivalents also fall into the scope defined by the appending claims of the present application.

The invention claimed is:

1. An antibody that binds human PD-1 (SEQ ID NO:1), comprising a light chain (LC) and a heavy chain (HC), wherein
the light chain comprises light chain complementarity determining regions LCDR1, LCDR2, and LCDR3 consisting of the amino acid sequences as set forth by SEQ ID NO:10, SEQ ID NO:11 and SEQ ID NO:12, respectively, and
the heavy chain comprises heavy chain complementarity determining regions HCDR1, HCDR2, and HCDR3, wherein
HCDR1 consists of the amino acid sequence as set forth by SEQ ID NO:2;
HCDR2 consists of the amino acid sequences as set forth by SEQ ID NO:3, SEQ ID NO:4, SEQ ID NO:5, SEQ ID NO:6, or SEQ ID NO:7; and
HCDR3 consists of the amino acid sequences as set forth by SEQ ID NO:8 or SEQ ID NO:9.

2. The antibody of claim 1, wherein HCDR1, HCDR2, and HCDR3 consist of:
(i) the amino acid sequences as set forth by SEQ ID NO:2, SEQ ID NO:3 and SEQ ID NO:8, respectively;
(ii) the amino acid sequences as set forth by SEQ ID NO:2, SEQ ID NO:4, and SEQ ID NO:9, respectively;
(iii) the amino acid sequences as set forth by SEQ ID NO:2, SEQ ID NO:5 and SEQ ID NO:8, respectively;
(iv) the amino acid sequences as set forth by SEQ ID NO:2, SEQ ID NO:6, and SEQ ID NO:8, respectively; or
(v) the amino acid sequences as set forth by SEQ ID NO:2, SEQ NO:7, and SEQ ID NO:9, respectively.

3. An antibody, comprising 1 or 2 light chain(s) (LC) and 1 or 2 heavy chain (s)(HC), wherein each of the light chain comprises a light chain variable region (LCVR) and each of the heavy chain comprises a heavy chain variable region (HCVR), wherein the LCVR has the amino acid sequence as set forth by SEQ ID NO:18, and the HCVR has the amino acid sequence as set forth by SEQ ID NO:13, SEQ ID NO:14, SEQ ID NO:15, SEQ ID NO:16 or SEQ ID NO:17.

4. The antibody of claim 3, wherein
   (i) the LCVR has the amino acid sequence as set forth by SEQ ID NO:18, and the HCVR has the amino acid sequence as set forth by SEQ ID NO:13;
   (ii) the LCVR has the amino acid sequence as set forth by SEQ ID NO:18, and the HCVR has the amino acid sequence as set forth by SEQ ID NO:14;
   (iii) the LCVR has the amino acid sequence as set forth by SEQ ID NO:18, and the HCVR has the amino acid sequence as set forth by SEQ ID NO:15;
   (iv) the LCVR has the amino acid sequence as set forth by SEQ ID NO:18, and the HCVR has the amino acid sequence as set forth by SEQ ID NO: 16; or
   (v) the LCVR has the amino acid sequence as set forth by SEQ ID NO: 18, and the HCVR has the amino acid sequence as set forth by SEQ ID NO: 17.

5. The antibody of claim 3, wherein the LC has the amino acid sequence as set forth by SEQ ID NO:24, and the HC has the amino acid sequence as set forth by SEQ ID NO:19, SEQ ID NO:20, SEQ ID NO:21, SEQ ID NO:22, or SEQ ID NO:23.

6. The antibody of claim 5, wherein
   (i) the LC has the amino acid sequence as set forth by SEQ ID NO:24, and the HC has the amino acid sequence as set forth by SEQ ID NO:19;
   (ii) the LC has the amino acid sequence as set forth by SEQ ID NO:24, and the HC has the amino acid sequence as set forth by SEQ ID NO:20;
   (iii) the LC has the amino acid sequence as set forth by SEQ ID NO:24, and the HC has the amino acid sequence as set forth by SEQ ID NO:21;
   (iv) the LC has the amino acid sequence as set forth by SEQ ID NO:24, and the HC has the amino acid sequence as set forth by SEQ ID NO:22; or
   (v) the LC has the amino acid sequence as set forth by SEQ ID NO:24, and the HC has the amino acid sequence as set forth by SEQ ID NO:23.

7. The antibody of claim 5, comprising two light chains and two heavy chains, wherein each light chain has the amino acid sequence as set forth by SEQ ID NO:24, and each heavy chain has the amino acid sequence as set forth by SEQ ID NO:19, SEQ ID NO:20, SEQ ID NO:21, SEQ ID NO:22, or SEQ 1D NO:23.

8. The antibody of claim 7, wherein
   (i) each light chain has the amino acid sequence as set forth by SEQ ID NO:24, and each heavy chain has the amino acid sequence as set forth by SEQ ID NO:19;
   (ii) each light chain has the amino acid sequence as set forth by SEQ ID NO:24 and each heavy chain has the amino acid sequence as set forth by SEQ ID NO:20;
   (iii) each light chain has the amino acid sequence as set forth by SEQ ID NO: 24, and each heavy chain has the amino acid sequence as set forth by SEQ ID NO:21;
   (iv) each light chain has the amino acid sequence as set forth by SEQ ID NO:24, and each heavy chain has the amino acid sequence as set forth by SEQ ID NO:22; or
   (v) each light chain has the amino acid sequence as set forth by SEQ ID NO:24, and each heavy chain has the amino acid sequence as set forth by SEQ ID NO:23.

9. The antibody of claim 7, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

10. The antibody of claim 1, wherein the antibody is glycosylated.

11. A culture comprising mammalian cell comprising a DNA molecule comprising a polynucleotide sequence encoding a polypeptide having the amino acid sequence of SEQ ID NO:24 and a polynucleotide sequence encoding a polypeptide having the amino acid sequence of SEQ ID NO:20, wherein the cell is capable of expressing an antibody comprising a light chain having the amino acid sequence of SEQ ID NO:24 and a heavy chain having the amino acid sequence of SEQ ID NO:20.

12. A process for producing an antibody comprising a light chain having the amino acid sequence of SEQ ID NO:24 and a heavy chain having the amino acid sequence of SEQ ID NO:20, comprising cultivating the mammalian cell of claim 11 under conditions such that the antibody is expressed, and recovering the expressed antibody.

13. An antibody produced by the process of claim 12.

14. A pharmaceutical composition, comprising the antibody of claim 1, and a pharmaceutical acceptable carrier.

15. A method of treating cancer, comprising step of administering to a subject in need with an effective amount of the antibody of claim 1.

16. The method of claim 15, wherein the cancer is melanoma, lung cancer, head and neck cancer, colorectal cancer, pancreatic cancer, gastric cancer, kidney cancer, bladder cancer, prostate cancer, breast cancer, ovarian cancer, or liver cancer.

17. The method of claim 15, further comprising administering simultaneously, separately, or sequentially one or more anti-tumor agents.

18. The method of claim 17, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

19. A pharmaceutical composition, comprising the antibody of claim 3, and a pharmaceutical acceptable carrier.

20. A method of treating cancer, comprising step of administering to a subject in need with an effective amount of the antibody of claim 3.

* * * * *